(12) United States Patent
Spector et al.

(10) Patent No.: US 6,586,440 B2
(45) Date of Patent: *Jul. 1, 2003

(54) PHARMACEUTICAL COMPOSITIONS OF 5-ALKYNYL URACIL COMPOUNDS

(75) Inventors: Thomas Spector, Durham, NC (US); David J. T. Porter, Raleigh, NC (US); Saad George Rahim, Beckenham (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/841,554

(22) Filed: Apr. 23, 2001

(65) Prior Publication Data

US 2001/0025033 A1 Sep. 27, 2001

Related U.S. Application Data

(63) Continuation of application No. 08/835,394, filed on Apr. 3, 1997, now Pat. No. 6,221,852, which is a continuation of application No. 08/336,717, filed on Nov. 9, 1994, now Pat. No. 5,643,913, which is a continuation of application No. 07/965,261, filed as application No. PCT/GB91/01197 on Jul. 18, 1991, now abandoned.

(30) Foreign Application Priority Data

Jul. 19, 1990 (GB) .............................................. 9015896
Nov. 17, 1990 (GB) .............................................. 9025039

(51) Int. Cl.$^7$ .......................................... A61K 31/505
(52) U.S. Cl. ...................................................... 514/274
(58) Field of Search ........................................ 514/274

(56) References Cited

U.S. PATENT DOCUMENTS

| | | |
|---|---|---|
| 4,124,765 A | 11/1978 | Kurono et al. |
| 4,381,344 A | 4/1983 | Rideout et al. |
| 4,719,214 A | 1/1988 | Shealy et al. |
| 4,863,927 A | 9/1989 | Tolman et al. |
| 5,643,913 A | 7/1997 | Spector et al. |

FOREIGN PATENT DOCUMENTS

| | | |
|---|---|---|
| DE | 2522369 C2 | 11/1988 |
| EP | 0 272 065 A2 | 6/1988 |
| EP | 0 337 599 A1 | 10/1989 |
| EP | 0 409 575 A1 | 1/1991 |
| JP | 0 371 139 A1 | 6/1990 |
| WO | 89/09603 | 10/1989 |

OTHER PUBLICATIONS

Fardos NM, Naguib et al., *Structure–Activity Relationship of Ligands of Dihydrouracil Dehydrogenase from Mouse Liver*, Biochemical Pharmacology38(9), 1471–1480 (1989).
Masaaki Iigo et al., *Enhancing Effect of Bromovinyldeoxyuridine on Antitumor Activity of 5'Deoxy5–Fluorouridine Against Adenocarcinoma 755 in Mice*, Biochemical Pharmacology, 38(12), 1885–1889 (1989).

Thornburg, Lora D. et al., *Mechanism–Based Inhibition of Thymine Hydroxylase*, J. American Chemical Society, 111, 7632–7633 (1989).
Kunihiko Tatsumi et al., *Inhibitory Effects of Pyrimidine, Barbituric Acid and Pyridine Derivatives on 5–Fluorouracil Degradation in Rat Liver Extracts*, Japan J. Cancer Research (Gann), 78, 748–55 (1987).
Desranges, C., *Chemical Abstracts*, 104:178920h, (1986).
Ho, Dah Hsi, *Chemical Abstracts*, 105:183337u, (1986).
Tuchman, M., *Chemical Abstracts*, 104:14633m, (1986).
Farkas, Jiri, *Synthesis of 1,2,4–Triazine–3,5(2H,4H)–Diones Containing Electronegative Substituents in Position 6*, Collection Czechosloval Chem. Commun., 48(9), 2676–2681 (1983).
Robins, Morris J. et al., *Nucleic Acid Related Compounds. 39.Efficient Conversion of 5–Iodo to 5–Alkynyl and Derived 5–Substituted Uracil Bases and Nucleosides*, J. Organic Chemistry, 48(11), 1854–62 (1983).
Kundu, Nitya G. et al., *Studies on Uracil Derivatives and Analogs. Synthesis of 5–(β–Trimethylsilyl) Ethynyluracil and 5–Ethynnyluracil*, J. Heterocyclic Chem., 19(3), 463–4 (1982).
Robins, Morris J. et al., *Nucleic Acid Related Compounds. 38. Smooth and high–yield iodination and chlorination at C–5 of uracil bases and p–toluyl–protected nucleosides*, Canada J. Chemistry, 60(5), 554–7 (1982).
Barr, Phillip J. et al., *Synthesis of Some 5–Halogenovinyl Derivative of Uracil and their Conversion into 2'–Deoxyribonucleosides*, Jr. Chemical Society Perkin Trans, 1(16), 1665–70 (1981).
Krenitsky, TA, et al., *Purine Nucleoside Sytnhesis, an Efficient Method Employing Nucleoside Phosphorylases*, Biochemistry, 20, 3615–3621 (1981).
Rogins, Morris J. et al., *Nucleic Acid Related Compounds. 31. Smooth and Efficient Palladium–Copper Catalyzed Coupling of Terminal Alkynes with 5–Iodouracil Nucleosides*, Tetrahedron Letters, 22(5), 421–4 (1981).
Bleackley, RC et al., *Replacement of the Iodine Atom of 5–Iodouracil by the 5–Cyano Group*, Nucleic Acid Chemistry, vol. 2, 927–30 (1978).
Hein, L. et al., *Preparation of 5–Trifluoromethyluracil*, Z. Chem., 17(11), 415–16 (1977).
Barr, P.J. et al., *Incorporation of 5–Substituted uracil Derivatives into Nucleic Acids, Part IV. The Synthesis of 5–Ehtynyluracil*, Nucleic Acids Research, 3(10), 2845 (1976).
Jones, AS et al., *A Method for the Rapid Preparation of 5–vinyluracil in High Yield*, Nucleic Acids Research, 1(1), 105–107 (1974).

(List continued on next page.)

*Primary Examiner*—William R. A. Jarvis
(74) *Attorney, Agent, or Firm*—John L. Lemanowicz

(57) ABSTRACT

This invention relates to pharmaceutical compositions of 5-alkynyluracil compounds in the form of tablets or capsules.

4 Claims, No Drawings

OTHER PUBLICATIONS

Sharma, et al., *Acetylenic Nucleosides. 3. Synthesis and Biological Activities of Some 5–Ethynylpyrimidine Nucleosides, Journal of Medicinal Chemistry*, 1984, vol. 27, No. 3, pp 410–412.

Berry, et al., *Modification of Radiation Effect on Mammalian Tumor Cells by Pharmacological Agents, Nature*, Oct. 13, 1962, No. 4850, vol. 196, pp 185–186.

Calabresi, et al, *Initial Clinical Studies with 5–Iodo–2'deoxyuridine, Cancer Research*, May 1961, vol. 21, pp. 550–559.

Erikson, et al., *Molecular Radiobiology of Human Cell Lines–V. Comparitive Radiosenstitizing Properties of 5–Halodeoxy–cytidines and 5–Halodeoxyuridines, Radiation Research*, 1963, vol. 20, pp. 252–262.

Szybalski, W., *X–Ray Sensitization by Halopyrimidines, Cancer Chemotherapy Reports*, Jul./Aug. 1974, Part 1, vol. 59 No. 4, pp. 539–557.

Erikson, et al., *Molecular Radiobiology of Human Cell Lines, Cancer Research*, Jan. 1963, vol. 23, pp. 122–130.

Abstract 88–307546/43 Astra AB, 1988.

Abstract 85–269830/44 Sloan–Kettering Inst, 1985.

Abstract 87–009180/02 Wellcome Foundation Ltd., 1987.

Abstract 87–095565/14 Wellcome Foundation Ltd., 1987.

Abstract 89–146562/20 Bristol Myers Co., 1989.

Jones, et al., *The Preparation and properties of Some 5–Substituted Uracil Derivatives, Nucleic Acids Research*, Spec. Pub. No. 1, pp 81 & 84, (1982).

Bobek, et al., *The Chemistry and Biology of Some New Nucleoside Analogs Active Against Tumor Cells, Chemistry and Biology of Nucleosides and Nucleotides*, pp. 135–149 (1978).

PHARMACEUTICAL COMPOSITIONS OF 5-ALKYNYL URACIL COMPOUNDS

This application is a continuation of Ser. No. 08/835,394, filed Apr. 3, 1997 and issued as U.S. Pat. No. 6,221,852, which is a continuation of Ser. No. 08/336,717, filed Nov. 9, 1994 and issued as U.S. Pat. No. 5,643,913, which is a continuation of Ser. No. 07/965,261, filed Jan. 19, 1993, now abandoned, which is a 371 of PCT GB91/01197 filed on Jul. 18, 1991.

The present invention relates to certain enzyme inactivators which are especially useful for co-administration with other therapeutic compounds such as antiviral compounds in order to provide an improved therapeutic index by reducing the toxic side-effects.

A therapeutic nucleoside analogue that has been found to have a particularly beneficial clinical effect against a spectrum of conditions associated with Human Immunodeficiency Virus (HIV) infections such as Acquired Immune Deficiency Syndrome (AIDS), AIDS-related complex (ARC) and asymptotomatic infections, is the compound 3'-azido-3'-deoxythymidine having the approved name zidovudine. This compound at low doses is generally very well tolerated by patients and is now widely used in the treatment of HIV infections. However, in certain patients treated with zidovudine, some haematogical suppression including anaemia and neutropenia may be observed, presumably arising from a certain limited level of toxicity of zidovudine observed towards stem cells. Other less commonly observed side-effects have been described such as myopathy which may be related to intracellular activity of zidovudine.

It has now been found that the stem cell and haematological toxicity of zidovudine can be reduced by co-administration of an inactivator of the enzyme uracil reductase (dihydropyrimidine dehydrogenase, EC 1.3.1.2) which reduces the degradation of uracil.

The present invention is thus based on the discovery that the use of an inactivator of uracil reductase in combination with zidovudine reduces the cellular toxicity of zidovudine.

According to the present invention therefore we provide a uracil reductase inactivator for use in medical therapy, especially in combination with zidovudine or a pharmaceutically acceptable salt or ester thereof, for example in the treatment or prophylaxis of HIV infections such as AIDS, ARC and asymptomatic infections.

The present invention further provides:

a) a combination of a uracil reductase inactivator and zidovudine or a pharmaceutically acceptable salt or ester thereof;

b) a method for the treatment or prophylaxis of an HIV infection in a human which comprises administering to the said human an effective anti-HIV amount of zidovudine or a pharmaceutically acceptable salt or ester thereof in combination with a uracil reductase inactivator.

It should be noted that the references herein to uracil reductase inactivators refer to compounds that inactivate the uracil reductase enzyme, effectively acting as suicide substrates, in contrast to compounds that merely have an inhibiting effect on the enzyme.

It has been found that particularly beneficial effects in reducing the toxicity of zidovudine have been achieved using as a uracil reductase inactivator a 5-substituted uracil compound, particularly a uracil compound substituted in the 5-position by a halogen atom e.g. iodine or bromine; a $C_{2-4}$ alkenyl group (e.g. vinyl) optionally substituted by halogen e.g. 2-bromovinyl, 1-chlorovinyl or 2-bromo-1-chlorovinyl; a $C_{2-6}$ alkynyl group optionally substituted by a halogen (e.g. bromine) atom; a cyano group; or a $C_{1-4}$ alkyl group substituted by halogen e.g. trifluoromethyl. Particularly preferred inactivators of uracil reductase for use in accordance with the invention are 5-ethynyluracil and 5-propynyluracil. Other inactivators for such use include:

5-ethynyluracil
5-cyanouracil
5-propynyluracil
5-bromoethynyluracil
5-(1-chlorovinyl)uracil
5-iodouracil
5-bromovinyluracil
5-hex-1-ynyluracil
5-vinyluracil
5-trifluorouracil
5-bromouracil
5-(2-bromo-1-chlorovinyl)uracil In experiments in mice, it has been found that red-blood cell anaemia induced by treatment with zidovudine could be at least partially prevented by treatment with 5-ethynyluracil.

The above 5-propynyluracil is a novel compound and represents a further feature of the present invention.

Other uracil reductase inactivators which may be employed in accordance with the present invention include compounds which generate the above uracil compounds in vivo. Such compounds include nucleoside derivatives which contain a nucleobase corresponding to the above 5-substituted uracil compounds, for example nucleoside derivatives containing a ribose, 2'-deoxyribose, 2',3'-dideoxyribose, arabinose or other cleavable sugar portion, which may additionally contain a 2'- or 3'-substituent such as halo, for example fluoro. Specific examples of such nucleoside derivatives are 1-(β-D-arabinofuranosyl)-5-prop-1-ynyluracil and 2',3',-dideoxy-5-ethynyl-3'-fluorouridine.

Zidovudine or a pharmaceutically acceptable salt or ester thereof and the said uracil reductase inactivator may be employed in combination in accordance with the invention by administration of the components of the combination to an appropriate subject either concomitantly, for example in a unitary pharmaceutical formulation, or, more preferably, separately, or sequentially within a sufficient time period whereby the desired therapeutic effect of the combination is achieved.

Zidovudine or a pharmaceutically acceptable salt or ester thereof and the uracil reductase inactivator may be administered respectively for therapy by any suitable route including oral, rectal, nasal, topical (including buccal and sublingual), vaginal and parenteral (including subcutaneous, intramuscular, intravenous and intradermal); the oral route is especially preferred. It will be appreciated that the preferred route will vary with the condition and age of the recipient, the nature of the infection and other clinical factors.

In general a suitable dose of zidovudine or a pharmaceutically acceptable salt or ester thereof will be in the range of 1.0 to 120 mg per kilogram body weight of the recipient per day, preferably in the range of 2 to 30 mg per kilogram body weight per day and most preferably in the range of 5 to 20 mg per kilogram body weight per day. The desired dose is preferably presented as two, three, four, five, six or more sub-doses administered at appropriate intervals throught the day. These sub-doses may be administered in unit dosage forms, for example, containing 10 to 1500 mg, preferably 20 to 1000 mg, and most preferably 50 to 700 mg of active ingredient per unit dosage form.

Experiments with 3'-azido-3'-deoxythymidine suggest that a dose should be administered to achieve peak plasma concentrations of the active compound of from about 1 to about 75 µM, preferably about 2 to 50 µM, most preferably about 3 to about 30 µM. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

The uracil reductase inactivator may be administered in a dosage in the range of 0.01 to 50 mg per kilogram body weight of the recipient per day, preferably in the range of 0.01 to 10 mg per kilogram body weight per day, most preferably in the range of 0.01 to 0.4 mg per kilogram body weight per day; an alternative preferred administration regime is 0.5 to 10 mg/kg once per week.

The desired dose is preferably presented as one, two or more sub-doses administered at appropriate intervals throughout the day. These sub-doses may be administered in unit dosage forms for example containing 1 to 200 mg, preferably 2 to 100 mg, most preferably 2 to 50 mg of the uracil reductase inactivator.

Zidovudine and the uracil reductase inactivator are employed in an appropriate ratio whereby the abovementioned toxic effects of zidovudine are reduced or obviated without significant reduction of the therapeutic effect of zidovudine; such a ratio (based on the respective weights of zidovudine and uracil reductase inactivator) is generally in the range 1:1 to 1000:1, preferably in the range 5:1 to 500:1 and particularly in the range 20:1 to 200:1.

Zidovudine and the uracil reductase inactivator are preferably administered in a pharmaceutical formulation, either in a single pharmaceutical formulation containing both components or in separate pharmaceutical formulations each containing one of the components of the combinations.

The present invention thus includes as a further feature a pharmaceutical formulation comprising a uracil reductase inactivator optionally in combination with zidovudine or a pharmaceutically acceptable salt or ester thereof together with at least one pharmaceutically acceptable carrier or excipient.

Each carrier must be "pharmaceutically acceptable" in the sense of being compatible with the other ingredients of the formulation and not injurious to the patient. Formulations include those adapted for oral, rectal, nasal, topical (including buccal and sublingual), vaginal and parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention adapted for oral administration may be presented as discrete units such as capsules, cachets or tablets each containing a predetermined amount of the active ingredient; as a powder or granules; as a solution or a suspension in an aqueous (at pH 10) or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethylcellulose), lubricant, inert diluent, preservative, disintegrant (eg. sodium starch glycollate, cross-linked povidone, crosslinked sodium carboxymethylcellulose) surface-active or dispersins agent. Moulded tablets may be made by moulding in a suitable machine a mixture of the powdered compound moistened with an inert liquid diluent. The tablets may optionally be coated or scored and may be formulated so as to provide controlled release of the active ingredient therein using, for example, hydroxypropylmethyl cellulose in varying proportions to provide the desired release profile.

Formulations for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulation for vaginal administration may be presented as pessaries, tampons, creams, gels, pastes, foams or spray formulations containing in addition to the active ingredient such carriers as are known in the art to be appropriate.

Formulations for parenteral administration include aqueous (at pH 10) and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

The above-mentioned uracil reductase inactivators which are employed in combination with zidovudine in accordance with the present invention may be prepared in conventional manner. For example, the inactivators referred to above may be prepared by the methods described in J. Heterocycl. Chem. 19(3) 463–4 (1982) for the preparation of 5-ethynyluracil; J. Chem. Soc. Perkin Trans. 1(16), 1665–70 (1981) for the preparation of 5-(2-bromovinyl)uracil, 5-bromoethynyluracil and 5-(2-bromo-1-chlorovinyl)uracil; Nucleic Acid Chemistry, Vol. 2, 927–30 (1978) for the preparation 5-cyanouracil; Nucleic Acids Research, 1(1) 105–7 (1974) for the preparation of 5-vinyluracil; Z. Chem. 17(11) 415–16 (1977) for the preparation of 5-trifluoromethyluracil; Nucleic Acids Research 3 (10), 2845 (1976) for the preparation of 5-(1-chlorovinyl)uracil.

The above nucleoside derivatives may also be prepared in conventional manner, for example in accordance with processes described in European Patent Specification No. 356166 for the preparation of 3'-fluoro-2', 3'-dideoxy-5- alkynyluridine compounds, such as 2',3'-dideoxy-5-ethynyl-3'-fluorouridine, and European Patent Specification No. 272065 for the preparation of 5-alkynyluracil arabinosides, such as 1(β-D-arabinofuranosyl)-5-prop-1-ynyluracil.

The novel 5-propynyluracil compound referred to above may be prepared by one of the following processes, namely:
a) treatment of a 5-propynyluridine compound to effect conversion thereof to the desired uracil compound; or
b) treatment of a uracil compound substituted in the 5-position by an appropriate leaving group with a propyne compound to give the desired uracil compound.

In the above process a), conversion may be effected by enzymatic means, for example by treatment of the uridine compound with a thymidine phosphorylase enzyme, advantageously in a buffered medium at a pH of 6 to 8.

In the above process b), a uracil compound substituted in the 5-position by a suitable leaving group e.g. iodo or bromo, is treated with a $C_{3-6}$ alkyne in the presence of an appropriate palladium catalyst such as bis(triphenylphosphine) palladium (II) chloride and cuprous iodide in an amine solvent such as triethylamine.

Other 5-substituted uracil compounds for use in accordance with the invention may be prepared in an analogous manner to those described above.

The following Examples illustrate the present invention.

EXAMPLE 1
5-Propynyluracil

A) To a stirred solution of 2'-deoxy-5-propynyluridine (European Patent Specification No. 272065) (20 g, 75 mmol) in aqueous phosphate buffer at pH 6.84 (1250 mL) was added purified E. coli thymidine phosphorylase (10,000 units) (T. A. Krenitsky et al, Biochemistry, 20, 3615, 1981; U.S. Pat. No. 4,381,344) and alkaline phosphatase (10,000 units) [Sigma type VII-S from bovine intestinal mucosa] and the whole mixture was incubated at 37° C. for 24 hours. The resulting white precipitate was filtered, washed with water (3×100 mL), ethanol (2×100 mL), ether (2×100 mL) and dried in vacuo over phosphorus pentoxide to give the title compound.
M.pt.: 275–280° C. (dec.).
$^1$H nmr δ ($d_6$DMSO) 11.5–11.0 (bs, 2H, NH), 7.61 (1H, s, H-6), 1.95 ppm (3H, s, $CH_3$).
Microanalysis calculated for $C_7H_6N_2O_2$: C, 56.00; H, 4.03; N, 18.66. Found: C, 55.92; H, 4.05; N, 18.77.

B) 1-Arabinofuranosyl-5-propynyluracil, (2.92 g, 20.4 mmoles), 200 ml aqueous potassium phosphate, pH 6, 8, 4,000 IU thymidine phosphorylase (Krenitsky, T. A. et al Biochemistry, 20, 3615, 1981 and U.S. Pat. No. 4,381,444), 4,000 IU uridine phosphorylase (Krenitsky, T. A. et al Biochemistry, 20, 3615, 1981 and U.S. Pat. No. 4,381,444) and 2,000 IU alkaline phosphatase (Boehringer Mannheim) were stirred at 40° C. for five days. Then 8,000 IU of thymidine phosphorylase, 20,000 IU uridine phosphorylase, 2,000 IU alkaline phosphatase and 30 IU acid phosphatase (Boehringer Mannheim) were added and incubation continued for an additional five days. 5-Propynyluracil, being less soluble than the nucleoside, precipitated from the reaction mixture.

The precipitate and liquid were dried in vacuo, then 5-propynyluracil was crystallized twice from hot water and vacuum dried at room temperature to give 0.92 g (6.1 mmoles) 5-propynyluracil in 59% yield.
$^1$H NMR δ (dDMSO) 11.2 ppm (bs, 2H, 1H and 3H), 7.6 ppm (1H, s, 6H), 1.95 ppm (3H, s $CH_3$).
CHN calculated for $C_7H_6N_2O_2$: C, 56.00; H, 4.03; N, 18.66. Analyzed at: C, 55.95; H, 4.03; N, 18.60.

UV spectra: in 0.1 M HCl max at 287 nm and 231 nm; in 50 mM potassium phosphate, pH 7.0 max at 287 nm and 231 nm; in 0.1 M NaOH max at 306 nm and 240 nm.
Mass spectrum gave peak at molecular ion weight of 151.

EXAMPLE 2
5-(Trimethylsilylethynyl)uracil

A solution of 5-iodouracil (8 g, 30 mmol) in redistilled triethylamine (500 mL) and dry DMF (10 mL) was degassed with oxygen-free nitrogen for 15 minutes. Bis(triphenylphosphine)palladium (II) chloride (0.5 g), copper (I) iodide (0.5 g) and trimethylsilylacetylene (10 g, 102 mmol) were then added and the mixture was heated with stirring at 50° C. for 24 hours. The cooled reaction mixture was filtered, the filtrate evaporated to dryness and the residue dissolved in dichloromethane (500 mL). The organic solution was washed with a 2% aqueous solution of disodium EDTA (3×250 mL), water (3×200 mL), dried ($Na_2SO4$) and evaporated to dryness. The residue was triturated with ethanol to give the first crop of the title compound. The solid filtered from the reaction mixture was also found to contain the required product but in a more impure form and so was worked up as above in a separate batch to give a second crop.
$^1$H nmr δ ($d_6$DMSO) 11.75–10.85 (2H, bs, NH), 7.75 (1H, s, H-6), 0.15 ppm (9H, m, $SiCH_3$).

EXAMPLE 3
5-Ethynyluracil

A solution of 5-(trimethylsilylethynyl)uracil (5.3 g, 25.4 mmol) in 0.2M solution of sodium methoxide in methanol (400 mL) was stirred at room temperature for 3 hours and neutralized to pH 7 with dilute hydrochloric acid. The precipitated product was filtered, washed with methanol and dried to give a first crop of the title compound. The filtrates and washings were combined, evaporated to dryness and the residue crystallised from methanol to give the second crop of product. Combination of both crops and a further recrystallisation from ethanol gave a pure product.
M.pt.: 260° C. (dec.).
$^1$H nmr δ ($d_6$DMSO) 11.6–10.8 (2H, bs, NH), 7.8 (1H, s, H-6), 4.03 ppm (1H, s, acetylenic H).
Microanalysis calculated for $C_6H_4N_2O_2$: C, 52.95; H, 2.96; N, 20.58. Found: C, 52.04; H, 2.92; N, 20.3.

EXAMPLE 4
a) 2,4-Dimethoxy-5-iodo-pyrimidine

A dry 1L round-bottomed flask was charged with 5-iodouracil (50 g, 0.21 mol), phosphorus oxychloride (300 ml), and N,N-diethylaniline (6 drops). The heterogenous mixture was heated in a 120° C. oil bath under a nitrogen atmosphere for 24 hours. The phosphorus oxychloride was distilled off (some product co-distills off). The reaction solution was next slowly and cautiously poured over ice (1L) and solid sodium bicarbonate keeping the internal temperature at or below −20° C. (This was accomplished by cooling in a dry-ice acetone bath). Once the addition was complete, the reaction mixture was adjusted to pH 7 by addition of solid sodium bicarbonate. The mixture was extracted with methylene chloride and the organic fractions dried by passage through phase separator paper. The crude solution of 2,4-dichloro-5-iodopyrimidine was immediately added dropwise to a solution containing MeOH (400 ml) and sodium methoxide (28.8 g, 0.533 mol). This addition took 1 hour. The reaction was then stirred at room temperature overnight. The solution was neutralized with $CO_2$ (gas), extracted with methylene chloride, dried over anhydrous $Na_2SO_4$ filtered and concentrated. The crude product was adsorbed onto silica gel (100 g) and loaded onto a 400 g silica gel flash chromatography column. The column was eluted with 90:10 hexanes: ethyl acetate (v:v). The appropriate fractions were combined and concentrated to a white solid as the title compound.
Yield 26.7 g (48%).
200 MHZ NMR CDCl$_3$ δ=3.97 (s, 3H); 4.02 (s, 3H), 8.43 (s, 1H).

b) 2,4-Dimethoxy-5-(β-trimethylsilyl)-ethynylpyrimidine

A dry 1L round-bottomed flask under a nitrogen atmosphere was charged with the product of stage a) (26.7 g, 0.10 mol), dry methylene chloride (Aldrich, 150 mL), dry Et$_3$N (freshly distilled from KOH pellets, 250 mL). The system was evacuated and purged with nitrogen several times via a Firestone valve. Trimethyl-silylacetylene (21.2 mL, 0.15 mol; Aldrich) was added by syringe. Next were added bis(triphenylphosphine)palladium (II) chloride (Aldrich 5.84 g, 8.32 mmol) and copper (I) iodide (Aldrich 4.76 g, 25 mmol). The mixture was heated in a 60° C. oil bath for 2 hours, cooled and filtered through Celite. The filtrate was concentrated in vacuo. The residue was diluted with toluene (100 mL) and then the toluene was removed in vacuo. The residue was taken up into methylene chloride (200 mL), filtered and the filtrate extracted with 5% aq. ethylenediaminetetraacetic acid, disodium salt dihydrate (3×100 mL Aldrich), H$_2$O (1×100 mL). The organic layer was dried via passage through phase separator paper and concentrated in vacuo. The product was purified on a Waters Prep 500 eluting with 95:5 hexanes: ethyl acetate (v:v). The crude product was adsorbed onto 100 g of silica gel and loaded onto a 400 g silica gel flash chromatography column. The column was eluted with 97.5:2.5 hexanes: ethyl acetate (v:v). The appropriate fractions were combined and concentrated.
Yield 16.94 g (73%).

A 1.2 g sample of the resulting compound was bound to 6 g of silica gel and loaded onto a 50 g flash chromatography column. The column was eluted with hexanes: ethyl acetate 95:5 (v:v). The appropriate fractions were combined, concentrated, stripped with CH$_2$Cl$_2$ (2×30 mL), and dried in vacuo to yield 1.000 g of the title compound, m.p. 72.5–73° C.
Lit. m.p. 73–74° C. J. Heterocyclic Chem., 19, 463 (1982).

c) 5-(β-trimethylsilyl)ethynyluracil

A dry 3-necked round-bottomed flask under nitrogen was charged with 2,4-dimethoxy-5-(β-trimethylsilyl) ethynylpyrimidine (6.5 g, 27.5 mmol), dry acetonitrile (120 mL Aldrich), sodium iodide (oven dried in vacuo 80° C., 18 h, 12.4 g, 82.7 mmol) and chlorotrimethylsilane (10.5 mL, 82.7 mmol freshly distilled). The mixture was heated at reflux for 3 hours and then concentrated in vacuo. The residue was digested with a solution containing methanol (40 mL) and water (20 mL) and the product filtered off to give 1.48 g (26%). The product was dissolved in chloroform and the solution adsorbed onto silica gel 7 g) which was then loaded onto a 35 g silica gel flash chromatography column. Elution with chloroform: methanol 95:5 (v:v) followed by chloroform: methanol 90:10 (v:v) and evaporation of the product-containing fractions yielded 1.23 g of the title compound as a white solid.

d) 5-Ethynyluracil

A solution containing 5-(β-trimethylsilyl)ethynyluracil (3.85 g, 18.4 mmol) and methanol (370 mL) was treated with a second solution containing sodium hydroxide (2.3 g, 57.5 mmol) and water (18 mL). The mixture was stirred at room temperature for 2 hours and then concentrated in vacuo. The residue was suspended in water (35 mL) and the pH adjusted to 5 using 0.1 N HCl. The solids dissolved and then a second precipitate formed when the pH=5. The product was filtered, washed with H$_2$O, and then dried in vacuo to give 2.3 g (92%) of 5-ethynyluracil as a light beige powder.
Microanalysis calculated for C$_6$H$_4$N$_2$O$_2$: C, 52.95: H, 2.96; N, 20.58. Found: C, 52.79; H, 3.02; N, 20.44.

EXAMPLE 5 a) 2',3'-5'-Tri-O-Acetyl-5-iodouridine

A dry 250 mL round-bottomed flask was charged with 5-iodouridine (10 g, 27 mmol Aldrich), anhydrous pyridine (30 mL) and acetic anhydride (30 mL). The reaction was stirred at room temperature for 30 minutes under a nitrogen atmosphere and the solvent removed in vacuo. The compound was diluted with toluene (2×50 mL) and the toluene removed in vacuo. The product was purified on a 75 g flash chromatrography column which was eluted with 90:10 (v:v) CHCl$_3$:MeOH. The appropriate fractions were combined and concentrated to give the title compound as a white foam. This was used directly in the next stage.

b) 2',3',5'-Tri-O-Acetyl-5-[2-(trimethylsilyl)ethynyl]uridine

A dry 1 L round-bottomed flask equipped with a reflux condenser (under N$_2$ atmosphere) was charged with the product of stage a) (27 mmol), dry methylene chloride (260 mL, Aldrich) and dry triethylamine (260 mL, freshly distilled from NaOH pellets). The system was evacuated and purged with nitrogen several times and remained under a nitrogen atmosphere. Next was added (trimethyl-silyl) acetylene (11.65 mL, 82 mmol; Aldrich) followed by copper (I) iodide (Aldrich, 1.57 g, 8.2 mmol) and bis (triphenylphosphine)palladium II chloride (Aldrich, 1.85 g, 2.6 mmol). The mixture was heated in a 60° C. oil bath for 30 minutes, cooled, and filtered. The filtrate was concentrated in vacuo. The residue was taken up into CH$_2$Cl$_2$(300 mL), filtered, washed with 5% aq. ethylenediaminetetraacetic acid, disodium salt (2×75 mL), H$_2$O (100 mL), dried over Na$_2$SO$_4$, filtered and concentrated in vacuo.

The resulting compound was bound to 50 g of silica gel and loaded onto a 400 g silica gel flash chromatrography column which was eluted with CHCl$_3$. The product fractions were combined and concentrated to yield the title compound as light yellow foam.
Yield 13 g.
300 MHz NMR CDCl$_3$ δ8.2 (br s, NH, 1H), 7.77 (s, 1H, H6), 6.11 (d, H1', 1H), 2.22 (s, 3H, OAc), 2.13 (s, 3H, OAc), 2.11 (s, 3H, OAc), 0.22 (s, 9H, SiMe$_3$).

c) 5-Ethynyluridine

The product of stage b) (9.5 g, 24 mmol) was dissolved in methanol (200 mL) and diluted with a solution containing sodium (0.8 g) and methanol (100 mL). The reaction was stirred at room temperature for 2 hours and was then neutralized using Dowex 50W-X8 (H$^+$ form) resin. The resin was removed by filtering and washed with methanol. The filtrate was concentrated in vacuo to give 4.85 g of a beige solid. The compound was purified on a Waters Prep 500 reverse phase C$_{18}$ column which was eluted with H$_2$O/ MeOH 85:15 (v:v) to give 1.2 g of the title product (white solid). Impure fractions were re-chromatographed. An additional 1.94 g of product were obtained.

Yield 49%.

| Calculated: | % C,49.25 | % H,4.47 | % N,10.44 |
| --- | --- | --- | --- |
| Found: | % C,49.07 | % H,4.53 | % N,10.32 |

200 MHz NMR (DMSOd$_6$) δ 11.60 (br s, NH, 1H), 8.36 (s, H6, 1H), 5.72 (d, J=4.3 Hz H1', 1H), 4.01 (s, 1H, C≡C—H).

The following Examples illustrate pharmaceutical formulations in which the "Active Ingredient" is 5-propynyluracil.

EXAMPLE 6

Tablet Formulations

The following formulations 6A, 6B and 6C are prepared by wet granulation of the ingredients (except the magnesium stearate) with a solution of the povidone followed by drying of the granules, addition of the magnesium stearate and compression.

|  | mg/tablet | mg/tablet |
| --- | --- | --- |
| Formulation 6A |  |  |
| Active ingredient | 5 | 2 |
| Lactose, B.P. | 205 | 75 |
| Povidone, B.P. | 15 | 10 |
| Sodium starch glycollate | 20 | 10 |
| Magnesium stearate | 5 | 3 |
|  | 250 | 100 |
| Formulation 6B |  |  |
| Active ingredient | 5 | 2 |
| Lactose, B.P. | 155 | — |
| Avicel PH 101 | 50 | 25 |
| Povidone, B.P. | 15 | 10 |
| Sodium starch glycollate | 20 | 10 |
| Magnesium stearate | 5 | 3 |
|  | 250 | 50 |
| Formulation 6C |  |  |
| Active ingredient | 5 |  |
| Lactose, B.P. | 205 |  |
| Starch | 50 |  |
| Povidone, B.P. | 6 |  |
| Magnesium stearate | 4 |  |
|  | 270 |  |

The following formulation 6D is prepared by direct compression of the admixed ingredients. The lactose used is of the direct compression type.

| Formulation 6D | mg/tablet |
| --- | --- |
| Active ingredient | 5 |
| Lactose | 155 |
| Avicel PH 101 | 100 |
|  | 260 |

The following formulation 6E is a controlled release tablet and is prepared by wet granulation of the ingredients (except magnesium stearate) with a solution of the povidone, followed by drying of the granules, addition of the magnesium stearate and compression.

| Formulation 6E | mg/tablet |
| --- | --- |
| Active ingredient | 5 |
| Hydroxypropylmethylcellulose (Methocel K4M Premium) | 110 |
| Lactose, B.P. | 50 |
| Povidone, B.P. | 28 |
| Magnesium stearate | 7 |
|  | 200 |

EXAMPLE 7

Capsule Formulations

The following formulations 7A and 7B are prepared by admixing the uncompressed ingredients and filling into a two-part hard gelatin capsule.

|  | mg/capsule |
| --- | --- |
| Formulation 7A |  |
| Active ingredient | 10 |
| Lactose, B.P. | 250 |
| Sodium starch glycollate | 25 |
| Magnesium stearate | 5 |
|  | 290 |
| Formulation 7B |  |
| Active ingredient | 5 |
| Pregelatinized starch NF15 | 245 |
|  | 250 |
| Formulation 7C |  |
| Active ingredient | 10 |
| Macrogol 4000, B.P. | 340 |
|  | 350 |

The Macrogol 4000 B. P. is melted and the active ingredient dispersed therein. The thoroughly mixed melt is then filled into a two-part hard gelatin capsule.

EXAMPLE 8

| Injectable Formulation |  |
| --- | --- |
| Active ingredient | 10 mg |
| Sterile, pyrogen free Pyrophosphate buffer (pH 10), q.s. to | 10 ml |

The active ingredient is dissolved in most of the pyrophosphate buffer (35–40° C.), then made up to volume and filtered through a sterile micropore filter into a 10 ml amber glass vial (type 1) and sealed with a sterile closure and overseal.

EXAMPLE 9

Suppository Formulation

|  | mg/suppository |
|---|---|
| Active ingredient, 63 μm* | 10 |
| Hard fat, B.P. (Witepsol H15-Dynamit Nobel) | 1790 |
|  | 1800 |

*The active ingredient is used as a powder wherein at least 90% of the particles are of 63 μm or less.

Our-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogeneous mix. The entire suspension is passed through a 250 μm stainless steel screen and, with continuous stirring, is allowed to cool to about 40° C. At a temperature of 38° C. to 40° C. 1.80 g. of the mixture is filled into suitable plastic moulds. The suppositories are allowed to cool to room temperature.

Determination of Uracil Reductase Inactivation

Uracil reductase (1 μM) (dihydropyrimidine dehydrogenase, EC 1.3.1.2) purified from bovine live was incubated with 100 μM inactivator and 5 mM dithiothreitol (enzyme reductant) at 37° for 30 minutes in 0.05 M Tris-HCL at pH 8.0. The enzyme and inactivator were diluted 100-fold into the assay buffer, which contained 200 μM NADPH, 200 μM thymine and 1 μM dithiothreitol in Tris-HCl at pH 8.0. The velocity of the enzyme was determined spectrophotometrically. These velocities have been corrected for NADPH oxidase activity, which was less than 10% of the rate of thymine-dependent oxidation of NADPH. The % inactivation of the enzyme was equal to 100% minus the percent of enzymatic activity remaining. Enzyme incubated without inhibitor was stable under these conditions. Parenthetical values are the relative first-order rate constants for inactivation of enzyme determined from similar experiments where the fractional activity was measured as a function of the time of incubation of 50 μM inactivator with enzyme.

The results are given below:

| Compound | % Inactivation | |
|---|---|---|
| 5-ethynyluracil | 100 | (100) |
| 5-cyanouracil[a] | 100 | (14) |
| 5-propynyluracil | 100 | (8) |
| 5-bromoethynyluracil | 100 | (8) |
| 5-(1-chlorovinyl)uracil | 100 | (5) |
| 5-iodouracil | 100 | (4) |
| 5-bromovinyluracil | 93 | |
| 5-hex-1-ynyluracil[a] | 90 | |
| 5-vinyluracil[a,b] | 86 | |
| 5-trifluorouracil | 75 | |
| 5-bromouracil | 75 | |
| 5-(2-bromo-1-chlorovinyl)uracil | 68 | |

[a]The inhibition was reversible since enzyme treated with this derivative slowly regained activity after a 100-fold dilution into the assay mixture.
[b]These nucleobases were generated in situ by treating the respective nucleosides with 40 units/ml of thymidine phosphorylase in 35 mM potassium phosphate for 20 minutes prior to addition to uracil reductase. The parent nucleosides were not inactivators.

Protection from Zidovudine Toxicity

Male mice were doses p.o. with 1000 mg/kg/day of zidovudine for 30 days either alone, or 1.5 hours after dosing with 2 mg/kg/day of 5-ethynyluracil (5-EU). Other groups of mice (a) were dosed with 2 mg/kg/day of 5-ethynyluracil alone; and (b) served as controls, receiving neither zidovudine nor 5-ethynyluracil. Levels of haematocrit, haemoglobin and red blood cells were determined.

The results are as follows:

| GROUP | HEMATOCRIT (%) | HEMOGLOBIN (g/dl) | RED BLOOD CELLS (million/ml) |
|---|---|---|---|
| Control | 48.1 | 16.0 | 9.7 |
| 5-EU | 45.9 | 15.1 | 9.1 |
| Zidovudine | 34.5 | 11.2 | 6.1 |
| Zidovudine plus 5-EU | 43.1 | 13.9 | 7.6 |

We claim:

1. A pharmaceutical composition comprising uracil substituted in the 5-position by $C_{2-4}$ alkynyl together with at least one pharmaceutically acceptable carrier, wherein the composition is a tablet or a capsule.

2. The pharmaceutical composition of claim 1, wherein the uracil substituted at the 5-position is present at an amount effective to inactivate uracil reductase.

3. The pharmaceutical composition of claim 1, wherein the uracil substituted at the 5-position is present at a dose of 1 to 200 mg.

4. The pharmaceutical composition of claim 1, wherein the uracil substituted at the 5-position is present at a dose of 2 to 50 mg.

* * * * *